US012502477B2

(12) United States Patent
Schwarz et al.

(10) Patent No.: US 12,502,477 B2
(45) Date of Patent: Dec. 23, 2025

(54) INFUSION PUMP WITH PIVOTABLE PERISTALTIC PUMP UNIT

(71) Applicant: B. Braun Melsungen AG, Melsungen (DE)

(72) Inventors: Jan Schwarz, Melsungen (DE); Matthias Schwalm, Schwalmstadt (DE); Mario Richardt, Zierenberg (DE); Daniel Weber, Lahrbach (DE); Joachim Schuetz, Fulda (DE); René Dietrich, Hofbieber (DE)

(73) Assignee: B. Braun Melsungen AG, Melsungen (DE)

(*) Notice: Subject to any disclaimer, the term of this patent is extended or adjusted under 35 U.S.C. 154(b) by 743 days.

(21) Appl. No.: 17/854,045

(22) Filed: Jun. 30, 2022

(65) Prior Publication Data

US 2023/0001079 A1 Jan. 5, 2023

(30) Foreign Application Priority Data

Jul. 1, 2021 (DE) ..................... 20 2021 103 512.9

(51) Int. Cl.
*A61M 5/142* (2006.01)

(52) U.S. Cl.
CPC ............................... *A61M 5/14228* (2013.01)

(58) Field of Classification Search
CPC .. A61M 5/14228; A61M 1/72; A61M 60/279; F04B 43/1276; F04B 43/1284
See application file for complete search history.

(56) References Cited

U.S. PATENT DOCUMENTS

| | | | | |
|---|---|---|---|---|
| 9,022,983 | B2 * | 5/2015 | Ueda | A61M 5/142 604/151 |
| 2011/0300010 | A1 * | 12/2011 | Jarnagin | A61B 17/3207 417/477.2 |

FOREIGN PATENT DOCUMENTS

| | | | |
|---|---|---|---|
| DE | 19729612 | C2 | 5/2001 |
| DE | 1020131032233 | A1 | 10/2014 |
| EP | 2716312 | A1 | 4/2014 |

* cited by examiner

*Primary Examiner* — Kami A Bosworth
*Assistant Examiner* — Nelson Louis Alvarado, Jr.
(74) *Attorney, Agent, or Firm* — Christopher A. Rothe; CM Law

(57) ABSTRACT

A linear peristaltic infusion pump has a pump housing to which a front lid is pivotably hinged to open and close the front lid. A peristaltic pump unit is pivotably received in the pump housing. A pivoting mechanism is functionally connected to the front lid to pivot the peristaltic pump unit backward into the pump housing when the front lid is open, and to pivot the peristaltic pump unit forward and away from the pump housing when the front lid is closed.

19 Claims, 6 Drawing Sheets

INFUSION PUMP WITH PIVOTABLE PERISTALTIC PUMP UNIT

CROSS-REFERENCE TO RELATED APPLICATION

This application claims priority under 35 U.S.C. § 119 to German Application No. 20 2021 103 512.9, filed Jul. 1, 2021, the content of which is incorporated by reference herein in its entirety.

FIELD

The present disclosure relates to an infusion pump based on the linear peristaltic principle, having a pump housing to which a front lid is pivotably hinged in order to open and close the front lid, and a peristaltic system/peristaltic pump unit/drive assembly pivotably received in the pump housing.

BACKGROUND

Developments in modern medicine, in particular in intensive care medicine, have led to infusion therapies that require the targeted use and precise dosing of highly effective medications. As part of these therapies, multiple medications and optionally parenteral nutrition often have to be administered, depending on the clinical picture. Thus, there is a need for modular infusion devices that are able to be easily equipped with multiple fluid pumps/infusion pumps. For this purpose, it is common practice to arrange the infusion pumps as a group during use in or on or via a carrying or holding device in order to ensure that the pumps can be operated and used as intended.

The pumps conventionally used for this purpose include infusion/peristaltic/tubing/tube-squeeze pumps. For the transport of an infusion solution, i.e. medication or parenteral nutrition, such an infusion pump usually uses a system based on linear peristalsis, which generates an essentially uniform flow of the infusion solution with low pulsation and variable strength. The drive is a peristaltic drive, which has a drive shaft and causes the compression of a defined volume/portion of an infusion tube inserted into the infusion pump during one shaft rotation of the drive shaft. By compressing the infusion tube, a desired amount of infusion solution can be conveyed/pumped. In order to produce the compression, the peristaltic system conventionally presses against a counter plate or pressure plate, which is usually accommodated in a front lid pivotably hinged to a housing that receives the peristaltic system.

Such peristaltic pumps are known from the prior art, for example DE 197 29 612 C2. There, a peristaltic pump with a movement device and several pump elements for progressive squeezing of the tube against a pressure surface is disclosed.

Furthermore, DE 10 2013 103 223 A1 also shows an infusion pump. This infusion pump has an infusion tube, a pump device which has at least one squeezing element which is provided for squeezing the infusion tube onto a counter bearing. Furthermore, the infusion pump has a clamping device which is configured to act on the pumping device and/or on the counter bearing in such a way that the squeezing pressure on the infusion tube changes as a function of a dynamic pressure present in the infusion tube during operation of the infusion pump.

Furthermore, an infusion pump is also disclosed in EP 2 716 312 A1. This infusion pump has a pump mechanism for pressing an infusion tube and supplying infusion fluid in the infusion tube in one direction, a pump body equipped with the pump mechanism, a door/front lid for covering an infusion-tube mounting position in the pump body in a freely opening and closing manner, and a door lock mechanism for locking the closed door.

With the known infusion pumps, insertion of the infusion tube is extremely difficult due to the limited space and the pressure exerted by the peristaltic system on an infusion-tube receiving portion.

SUMMARY

Therefore, the objects and objectives of the disclosure are to overcome or at least reduce the disadvantages of the prior art and, in particular, to provide an infusion pump that improves handling of the infusion pump during insertion of the infusion tube.

Accordingly, the infusion pump is according to the disclosure configured by a pivoting mechanism which is functionally, in particular mechanically or electronically/electrically, connected to the front lid so as to pivot the peristaltic pump unit backward into the pump housing, away from to the front lid when the front lid is open or opening and forward, away from the pump housing when the front lid is closed or closing.

This ensures that during the insertion process, i.e. with the front lid open, the peristaltic system does not press on the infusion-tube receiving portion, so that the infusion tube can be easily inserted into it.

In other words, the pivot mechanism can be coupled to the front lid via a transmission/lever/joint mechanism (i.e. mechanically) in such a way that an opening movement of the front lid is transformed into a pivoting movement of the peristaltic pump unit toward the rear and a closing folding movement of the front lid is transformed into a pivoting movement of the peristaltic pump unit toward the front. Alternatively, however, it is also possible to provide an (electric) drive which actuates the pivoting movements of the peristaltic pump unit and to couple this to a sensor/switch/motion detector etc. which registers opening and closing or an opening and closing position and switches the drive in a corresponding drive direction.

In a preferred embodiment, the peristaltic pump unit may be arranged in a peristaltic frame arranged stationarily in the pump housing so as to be pivotably arranged relative thereto.

It may also be advantageous if the infusion pump has an adjustable spring element, preferably in the form of a wave spring, which presses the peristaltic pump unit forward. Preferably, a spring force of the spring element on the peristaltic pump unit can be adjustable via an adjustment device, in particular in the form of a screw.

According to an advantageous further development, the pivoting mechanism may have a deadbolt (slide link), which moves in the longitudinal direction of the front lid in order to lock and unlock the front lid.

The deadbolt may have at least one, preferably three, guide groove(s) in which a (respective) closing pin of the front lid engages when the front lid is closing.

In addition, it may be practical if the peristaltic pump unit has a first wedge portion on which a second wedge portion of the deadbolt slides when the front lid is closing.

In addition, it may be advantageous if a wedge tip of the first wedge portion presses on a wedge tip of the second wedge portion when the front lid is open.

Preferably, the deadbolt may comprise an essentially L-shaped reset element which comprises/forms the second wedge portion. Particularly preferably, the reset element may be configured as an injection-molded plastic part and the second wedge portion may have a reinforcing structure made of metal.

BRIEF DESCRIPTION OF THE DRAWING FIGURES

The disclosure is explained in more detail below with reference to a preferred configuration example with the aid of figures, of which:

The figures are schematic in nature and serve only to aid understanding of the disclosure. Identical elements are provided with the same reference signs.

DETAILED DESCRIPTION

Figure 1:
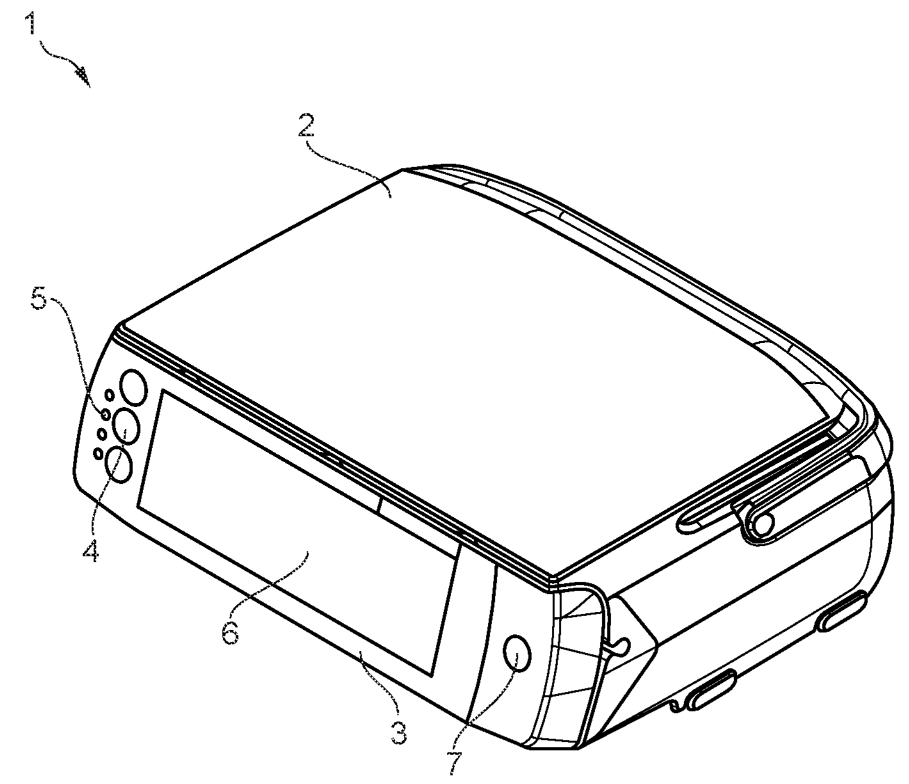
FIG. 1 shows a perspective view of a medical infusion pump according to the disclosure, in accordance with a preferred configuration example.

FIG. 1 shows a medical infusion pump 1 according to a preferred configuration example.

As shown in FIG. 1, the infusion pump 1 has an essentially cuboid pump housing 2 with a front lid/door 3 pivotably hinged to the front of the pump housing. A plurality of operating buttons 4, a plurality of signal lights 5, and a touch display 6 are arranged on a front side of the front lid 3. In addition, the front lid 3 has a front lid opening button 7 via which the front lid 3 can be opened or unlocked, as explained in more detail below, in order to enable a pivoting movement of the front lid in the opening direction.

Figure 2:
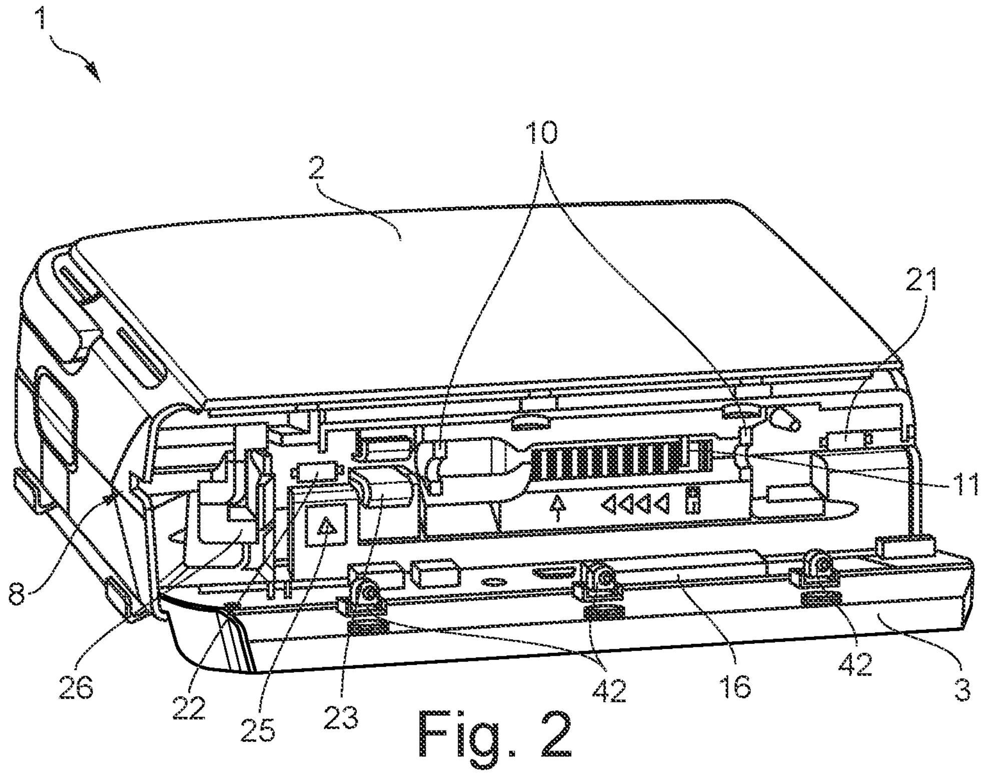
FIG. 2 shows a perspective view of the infusion pump according to the preferred configuration example with a front lid in an open state.

The front lid 3 is hinged to the pump housing 2 in such a way that, in an open state shown in FIG. 2, it folds downward to expose a tube passage 8 formed on a front side/front of the pump housing 2. An infusion tube/disposable item 9 (cf. FIG. 3) can be inserted into the tube passage 8 in order to convey/pump a medical fluid via the infusion pump 1 through the infusion tube 9. For this purpose, in the preferred configuration example, the tube passage 8 has two snap-in receptacles or snap-in interfaces 10 into which corresponding snap-in means or snap-in mating interfaces connected to the infusion tube 9 can engage, thereby securing the infusion tube 9 to the tube passage 8. As shown in FIG. 2, the snap-in receptacles 10 are formed on a slide guide 11 in the preferred configuration example. The slide guide 11 is configured to be removable, i.e. the slide guide 11 can be detached from the pump housing 2 and removed. A membrane 12 (cf. FIG. 5) is arranged on a rear side of the slide guide 11, i.e. a side facing away from the front lid 3, wherein a plurality of membrane openings 13 are formed in this membrane 12. During operation of the infusion pump 1, squeezing elements/peristaltic fingers 14 (cf. FIG. 3 or 4) of a peristaltic pump unit 15 engage in these membrane openings 13 (cf. FIG. 5) in order to exert pressure on the slide guide 11 and to squeeze the infusion tube 9 section by section. For this purpose, the squeezing elements 14 can be moved out of the peristaltic pump unit 15 (cf. FIG. 3) to different extents, as can be seen in FIG. 5, in order to squeeze the infusion tube 9 section by section and to convey the medical fluid through the infusion tube 9, as described in more detail below.

Figure 3:
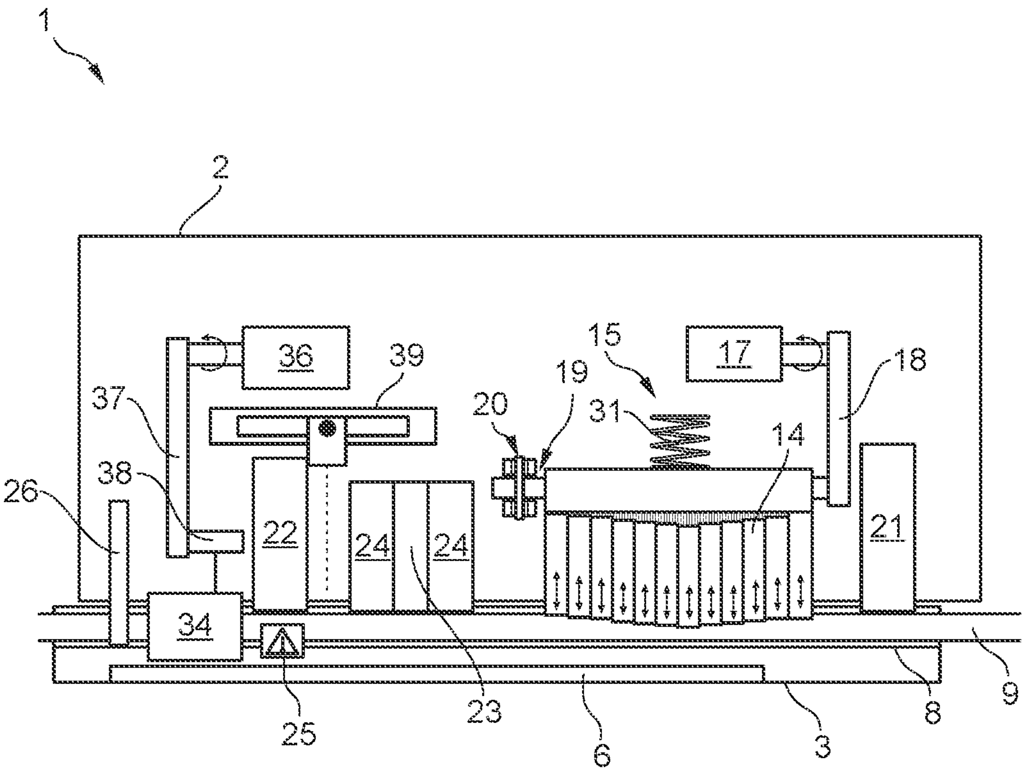
FIG. 3 shows a block diagram of the infusion pump according to the preferred configuration example.

FIG. 3 is a block diagram of the infusion pump 1 according to the preferred configuration example. It can be seen that the squeezing elements 14 of the peristaltic pump unit 15 press the inserted infusion tube 9 section by section against a counter plate 16 (cf. FIG. 2) arranged on the front lid 3 in order to squeeze the infusion tube 9 in the maximum extension, i.e. when the squeezing elements 14 are moved out to the maximum, in such a way that an occlusion forms in the infusion tube 9. In order to move out the squeezing elements 14, the peristaltic pump unit 15 further comprises a drive motor 17, which transmits its drive power via a transmission 18 to a drive shaft 19. In the preferred configuration example, this drive shaft 19 is in the form of a camshaft so that the squeezing elements 14 can be moved out to different extents when the drive shaft 19 rotates. In addition, the drive motor 17 or the drive shaft 19 is monitored for speed and direction of rotation by at least one drive sensor 20.

As shown in FIGS. 2 and 3, an upstream pressure sensor 21 is arranged on the front side of the pump housing 2 upstream (on the right side in FIGS. 2 and 3) of the slide guide 11 or of the peristaltic pump unit 15 arranged behind it. The upstream pressure sensor 21 is arranged on an access side to the infusion tube 9 and monitors the pressure within the infusion tube 9 upstream of the slide guide 11. Downstream of the slide guide 11, a downstream pressure sensor 22 is arranged, which is arranged on an access side to the patient and monitors the pressure within the infusion tube 9 downstream of the slide guide 11.

An air sensor 23 is also arranged between the slide guide 11 and the downstream pressure sensor 22 to monitor possible air pockets or respectively to detect possible air bubbles in the infusion tube 9. Furthermore, two temperature sensors 24 are placed in the area of the air sensor 23 to monitor a temperature of the medical fluid inside the infusion tube 9. Alternatively air sensors and temperature sensors may be formed as a single unit. As can be seen in FIG. 2, a warning light 25 is formed below the downstream pressure sensor 22. This warning light 25 indicates whether a slide clamp 26 located downstream of the downstream pressure sensor 22 is open or closed. In normal operation of the infusion pump 1, the slide clamp 26 is fully pulled onto the infusion tube 9 when the front lid 3 is opened, i.e. the slide clamp 26 clamps the infusion tube 9 so that fluid can no longer flow through the infusion tube 9 to a downstream side of the slide clamp 26. Consequently, the warning light 25 lights up or flashes when the slide clamp 26 is open with the front lid 3 open.

Figure 4:
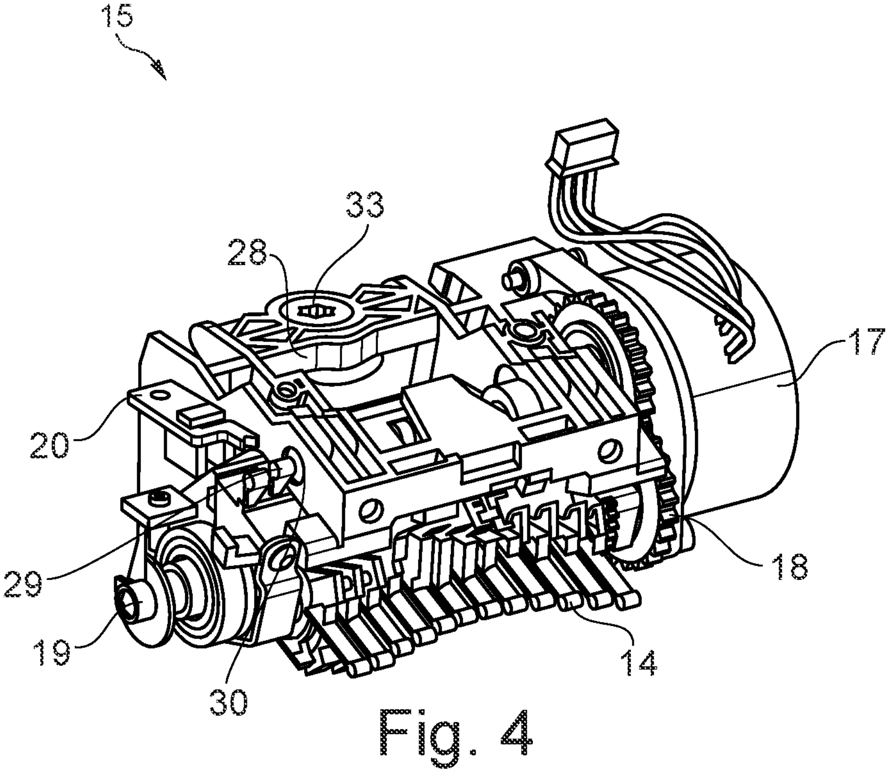
FIG. 4 shows a perspective view of a peristaltic pump unit of the infusion pump according to the preferred configuration example.
Figure 5:
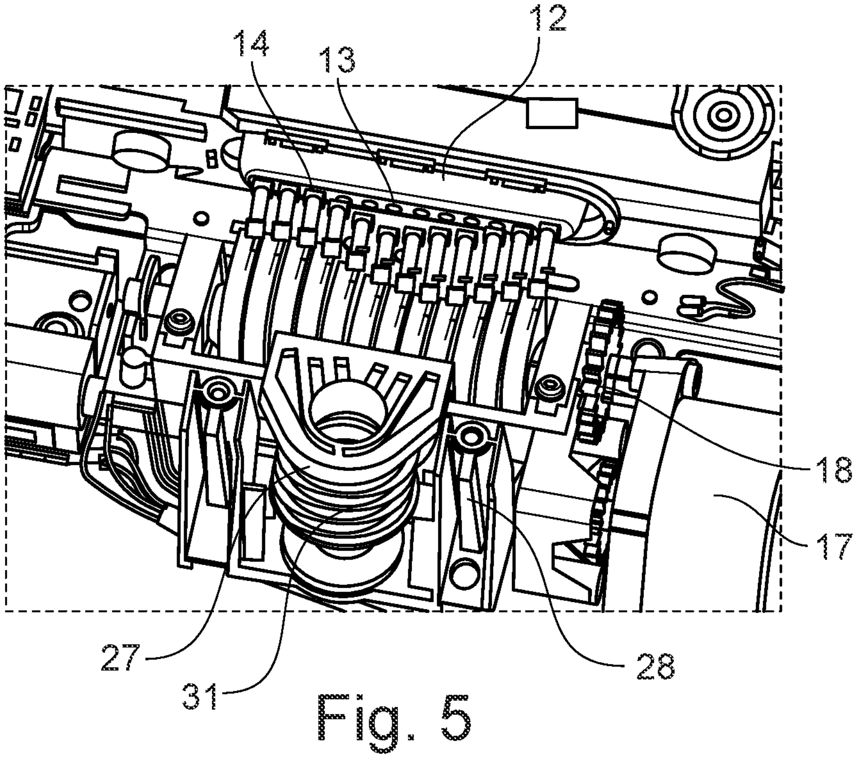
FIG. 5 shows a perspective view of the peristaltic pump unit in an installed state.
Figure 9:
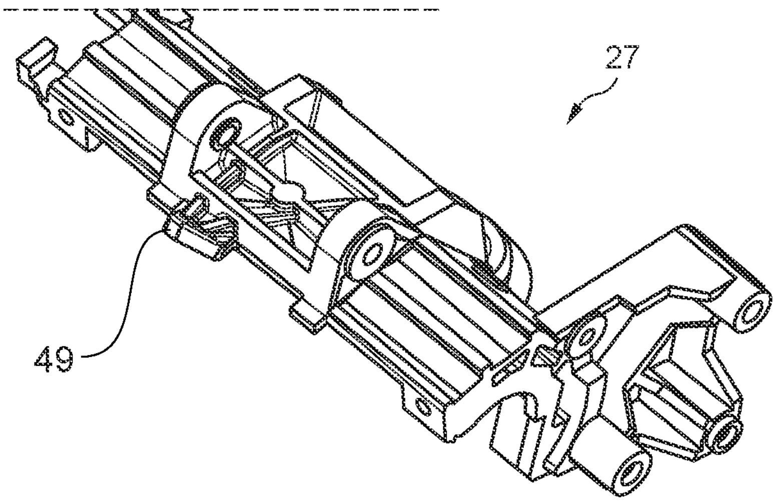
FIG. 9 shows a perspective view of a swinging link of the peristaltic pump unit of the infusion pump according to the preferred configuration example.

In FIG. 4, the peristaltic pump unit 15 is shown in a removed/disassembled state. As mentioned above, the peristaltic pump unit 15 has the squeezing elements 14 driven by the drive shaft 19. The drive shaft 19 is stationary in a swinging link 27 (see FIG. 9), which in turn is pivotably received in a peristaltic frame 28. The peristaltic frame 28 is screwed to the pump housing 2, as shown for example in FIG. 6. In other words, the peristaltic frame 28 is stationarily received in the pump housing 2 so that the swinging link 27 together with the drive components, i.e. drive motor 17, transmission 18, drive shaft 19 and the squeezing elements 14 stationarily attached thereto, can be deflected relative to the pump housing 2. For this purpose, the swinging link 27 is supported on a shaft 29, which is received in corresponding bearing bores 30 in the peristaltic frame 28. Thus, the peristaltic pump unit 15 can be deflected in the pump housing 2 toward the front lid 3 or away from the front lid 3, respectively. In other words, the peristaltic pump unit 15 can pivot forward, away from the pump housing 2, i.e., toward the front lid 3, and rearward into the pump housing 2, i.e., away from the front lid 3.

Figure 6:
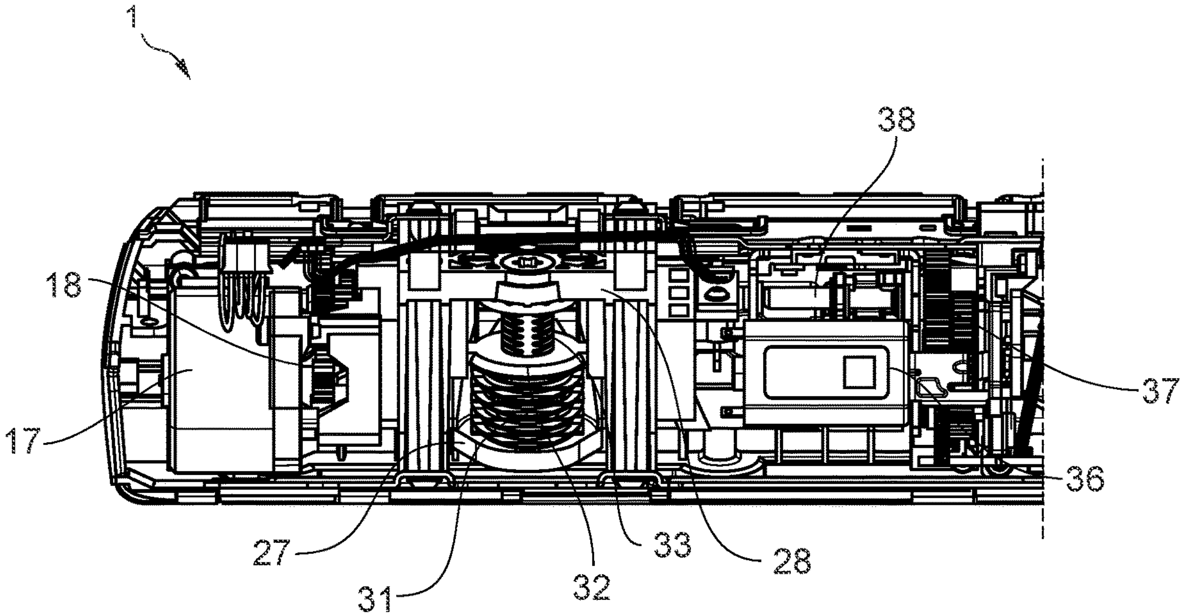
FIG. 6 shows a perspective rear view of the peristaltic pump unit in the installed state.

Furthermore, the peristaltic pump unit 15, as shown in FIGS. 5 and 6, has a wave spring 31 on a side facing away from the squeezing elements 14, which tensions/presses the swinging link 27 against the peristaltic frame 28, i.e. against the pump housing 2. The wave spring 31 is arranged between the swinging link 27 and the peristaltic frame 28 in such a way that the swinging link 27 is pressed or pivoted forward toward the front lid 3 due to the spring force of the wave spring 27. For this purpose, the wave spring 31 presses on a counter-pressure plate 32 received in the peristaltic frame 28. The counter-pressure plate 32 has an internal thread into which an adjustment screw 33 can be screwed to adjust the spring force of the wave spring 31. A screw head of the adjustment screw 33 is held in the peristaltic frame 28 in an axial extension direction of the adjustment screw 33. The counter-pressure plate 32 (FIG. 6), in turn, is provided movable in the axial extension direction of the adjustment screw 33 relative to the peristaltic frame 28. As a result, the counter-pressure plate 32 can move in the axial extension direction of the adjustment screw 33 when the adjustment screw 33 rotates, in order to compress or relieve the wave spring 31 or, respectively, to adjust the spring force acting on the swinging link 27.

Figure 7:
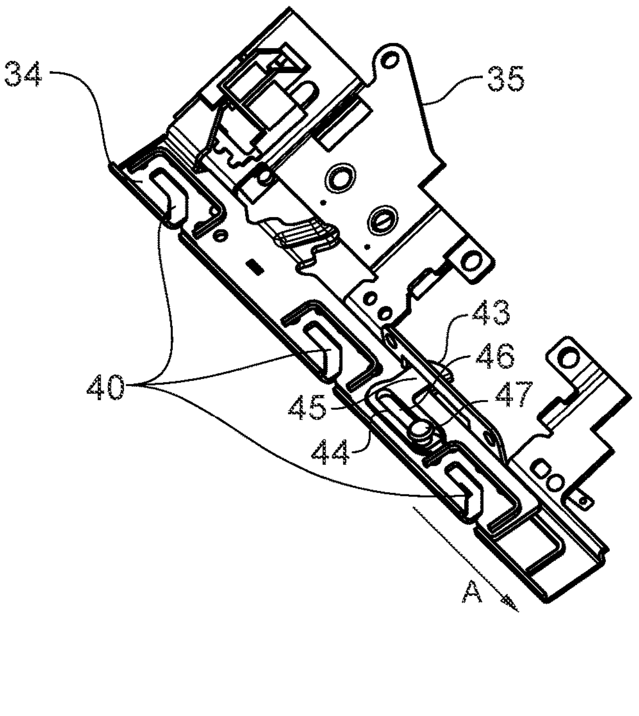
FIG. 7 shows a perspective view of a deadbolt of the infusion pump according to the preferred configuration example.

As mentioned above, the front lid 3 is pivotably hinged to the pump housing 2 to pivot between the open and closed states. In order to keep the front lid 3 in the closed state, i.e. to lock the front lid 3, the infusion pump 1 has a locking mechanism in the form of a deadbolt 34 shown in FIG. 7. Here, the deadbolt 34 is housed in the pump housing 2 such that it can move in a longitudinal direction of the front lid, i.e., the deadbolt 34 can move in the longitudinal direction of the front lid relative to the front lid 3 and the pump housing 2. For this purpose, as shown in FIG. 7, the deadbolt 34 is arranged on an inner frame 35 stationarily fixed in the pump housing 2. In other words, the deadbolt 34 can move relative to the inner frame 35 in the longitudinal direction of the front lid.

As is clear from the block diagram in FIG. 3 and in FIG. 6, the deadbolt 34 has a deadbolt drive motor 36 for this purpose, which drives a deadbolt displacement mechanism 38 via a deadbolt gear range 37. In the preferred configuration example, the deadbolt displacement mechanism 38 is configured as a spindle drive which drives a spindle nut attached to the deadbolt 34. For determining the position of the deadbolt 34, the infusion pump 1 has a deadbolt position sensor 39 (FIG. 3). This deadbolt position sensor 39 is configured as a linear potentiometer in the preferred configuration example, in order to be able to detect the exact position of the deadbolt 34.

Furthermore, in the preferred configuration example, the deadbolt 34 has three arcuate guide grooves 40, each of which opens on a side of the deadbolt 34 facing the front lid 3 and describes an arc of approximately 90° from there before extending for a short portion approximately parallel to the longitudinal direction of the front lid. As shown in FIG. 7, the inner frame 35 has three frame grooves 41 (cf. FIG. 8), which also open on a side of the inner frame 35 facing the front lid 3 and extend from there to the rear, i.e. away from the front lid 3.

Figure 8:
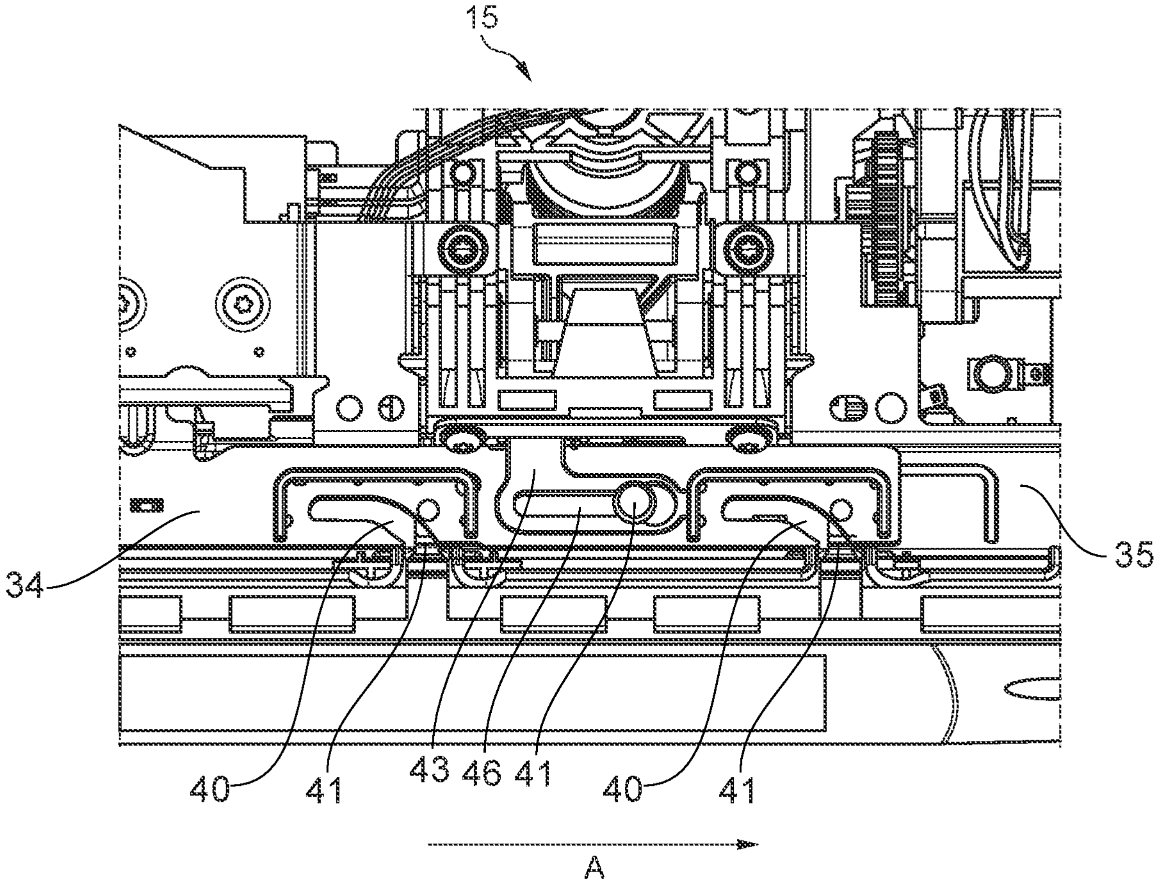
FIG. 8 shows a partial view of the infusion pump according to the preferred configuration example.

FIG. 7 or FIG. 8 shows the deadbolt 34 in the open state of the front lid 3. The openings of the guide grooves 40 and the openings of the frame grooves 41 lie on top of each other or are aligned, respectively, as shown in FIG. 8. If the front lid 3 is now to be closed, it first has to be folded manually toward the pump housing 2 until the closing pins 42 formed on the front lid 3 engage in the openings of the guide grooves 40 and the openings of the frame grooves 41. The closing pins 42 of the front lid 3 can be seen in FIG. 2. As soon as the closing pins 42 engage in the guide grooves 40 and the frame grooves 41, the deadbolt drive motor 36 moves the deadbolt 34 in a locking direction A so that the closing pins 42 are guided in the guide grooves 40 and are thus locked. In other words, the front lid 3 closes automatically after the front lid 3 is pressed against the pump housing 2.

In order to be able to open the front lid 3 again, it first has to be unlocked. In order to do this, the front-lid opening button 7 on the front lid 3 is pressed/actuated, which causes the deadbolt drive motor 36 to move the deadbolt 34 reverse to the locking direction A in order to release the closing pin 42 and to open the front lid 3.

As can be seen in FIG. 7, an essentially L-shaped reset element 43 is arranged on the deadbolt 34 in such a way that a first portion 44 of the reset element 43 extends essentially parallel to the longitudinal direction of the front lid, and a second portion 45 of the reset element 43 projects backward perpendicularly from the first portion 44. A guide groove 46 is formed in the first portion 44, in which a guide bolt 47, in particular a riveted guide bolt, connected to the inner frame 35 is guided. If the deadbolt 34 is moved in or reverse to the locking direction A, as explained above, the guide bolt 47 is also displaced relative to the guide groove 46. The second portion 45 of the reset element 43 protrudes through a recess in the inner frame 35 onto a rear side of the inner frame 35 facing away from the front lid 3, as shown in FIG. 7. An end portion of the second portion 45 projecting onto the rear side of the inner frame 35 is formed in the shape of a wedge portion 48 (see FIG. 10). That is, the end portion of the second portion 45 describes a ramp such that the front surface of the second portion 45 is provided forming an angle at the end portion of the second portion 45. In the preferred configuration example, the reset element 43 is configured as an injection-molded plastic part, wherein the wedge portion 48 (cf. FIG. 9) has a metallic reinforcing structure in its interior and/or a metallic end surface.

Figure 10:
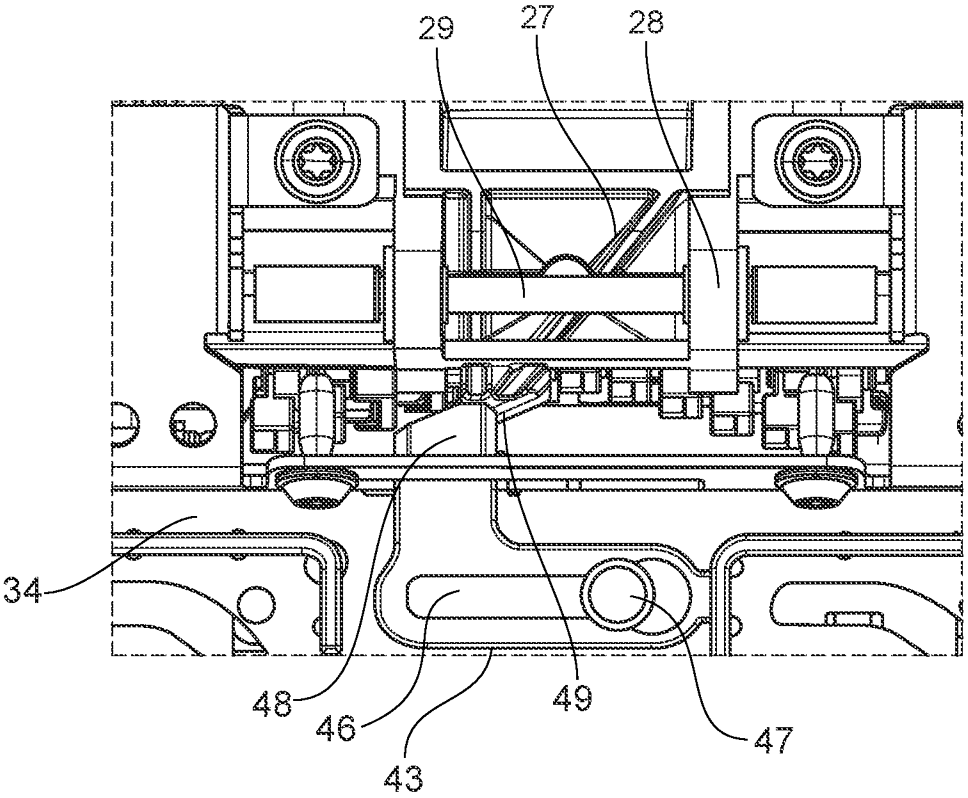
FIG. 10 shows a partial perspective view of a pivoting mechanism of the infusion pump according to the preferred configuration example.

The wedge portion 48 of the reset element 43 extends beyond the inner frame 35 such that it is in contact with a wedge portion 49 of the swinging link 27, as shown in FIG. 10. In other words, the wedge portions 48, 49 of the reset element 43 and of the swinging link 27 press against each other, wherein in the opened state of the front lid 3, a tip of the wedge portion 48 presses against a tip of the wedge portion 49. When the tips of the wedge portions 48, 49 are in contact with each other, the reset element 43 pushes the swinging link 27 backward into the pump housing 2 against the spring force of the wave spring 31. This means that when the front lid is open, the swinging link 27 and thus the peristaltic pump unit 15 are swung backward into the pump housing 2 by the deadbolt 34.

When the front lid 3 is now being closed, the deadbolt 34 moves in the locking direction A (to the right in FIG. 10) so that the wedge portion 48 slides off the wedge portion 49. This allows the swinging link 27 to swing forward toward the front lid 3 due to the spring force of the wave spring 31, so that the squeezing elements 14 enter the membrane opening 13.

The invention claimed is:

1. An infusion pump comprising:
- a pump housing extending from a front end to a back end;
- a front lid pivotably hinged to the front end of the pump housing in order to open and close the front end of the pump housing;
- a peristaltic pump unit pivotably received in the pump housing; and
- a pivoting mechanism connected to the front lid,
- the peristaltic pump unit being a linear peristaltic pump,
- the pivoting mechanism being configured to pivot the peristaltic pump unit backward towards the back end of the pump housing when the front lid is opened, and
- the pivoting mechanism being configured to allow the peristaltic pump unit to pivot forward towards the front end of the pump housing when the front lid is closed.

2. The infusion pump according to claim 1, wherein the peristaltic pump unit is arranged in a peristaltic frame arranged stationarily in the pump housing so as to be pivotably arranged relative to the pump housing.

3. The infusion pump according to claim 1, further comprising an adjustable spring element that presses the peristaltic pump unit forward towards the front end of the pump housing when the front lid is closed.

4. The infusion pump according to claim 3, wherein the adjustable spring element is a wave spring.

5. The infusion pump according to claim 3, wherein a spring force of the adjustable spring element is adjustable via an adjustment device.

6. The infusion pump according to claim 5, wherein the adjustment device is a screw.

7. The infusion pump according to claim 1, wherein the pivoting mechanism has a deadbolt which moves in a longitudinal direction of the front lid to lock and unlock the front lid.

8. The infusion pump according to claim 7, wherein the deadbolt has at least one guide groove in which a closing pin of the front lid engages when the front lid is closing.

9. The infusion pump according to claim 7, wherein the peristaltic pump unit has a first wedge portion on which a second wedge portion of the deadbolt slides when the front lid is closing.

10. The infusion pump according to claim 9, wherein a first wedge tip of the first wedge portion presses on a second wedge tip of the second wedge portion when the front lid is open.

11. The infusion pump according to claim 9, wherein the deadbolt has a reset element that is L-shaped, the reset element comprising the second wedge portion.

12. The infusion pump according to claim 11, wherein the reset element is an injection-molded plastic part and the second wedge portion has a reinforcing structure made of metal.

13. The infusion pump according to claim 1, wherein the peristaltic pump unit comprises a drive motor, and the pivoting mechanism is configured to pivot the peristaltic pump unit including the drive motor backward towards the back end of the pump housing when the front lid is opened.

14. An infusion pump comprising:
- a pump housing extending from a front end to a back end;
- a front lid pivotably hinged to the front end of the pump housing in order to open and close the front end of the pump housing;
- a peristaltic pump unit pivotably received in the pump housing; and
- a pivoting mechanism connected to the front lid,
- the peristaltic pump unit being a linear peristaltic pump,
- the pivoting mechanism being configured to pivot the peristaltic pump unit backward towards the back end of the pump housing when the front lid is opened, and
- the pivoting mechanism being configured to allow the peristaltic pump unit to pivot forward towards the front end of the pump housing when the front lid is closed,
- wherein the pivoting mechanism has a deadbolt which moves in a longitudinal direction of the front lid to lock and unlock the front lid.

15. The infusion pump according to claim 14, wherein the deadbolt has at least one guide groove in which a closing pin of the front lid engages when the front lid is closing.

16. The infusion pump according to claim 14, wherein the peristaltic pump unit has a first wedge portion on which a second wedge portion of the deadbolt slides when the front lid is closing.

17. The infusion pump according to claim 16, wherein a first wedge tip of the first wedge portion presses on a second wedge tip of the second wedge portion when the front lid is open.

18. The infusion pump according to claim 16, wherein the deadbolt has a reset element that is L-shaped, the reset element comprising the second wedge portion.

19. The infusion pump according to claim 18, wherein the reset element is an injection-molded plastic part and the second wedge portion has a reinforcing structure made of metal.

* * * * *